United States Patent [19]

Lysenko et al.

[11] Patent Number: 5,463,129
[45] Date of Patent: Oct. 31, 1995

[54] CLEAVING ARYLETHERS

[75] Inventors: Zenon Lysenko; Richard G. Pews, both of Midland, Mich.

[73] Assignee: The Dow Chemical Company, Midland, Mich.

[21] Appl. No.: 173,451

[22] Filed: Dec. 23, 1993

[51] Int. Cl.$^6$ .................................................. C07C 211/50
[52] U.S. Cl. ..................... 564/423; 564/414; 568/763; 568/774; 568/796; 568/805
[58] Field of Search .................................. 568/763, 762, 568/805, 774, 796; 564/423

[56] References Cited

U.S. PATENT DOCUMENTS

| | | | |
|---|---|---|---|
| 4,766,244 | 8/1988 | Lysenko | 564/418 |
| 4,912,246 | 3/1990 | Lysenko et al. | 558/269 |
| 5,072,053 | 12/1991 | Blank et al. | 568/586 |

FOREIGN PATENT DOCUMENTS 02229143  9/1990  Japan .

OTHER PUBLICATIONS

"Hydroxylation of Nitroarenes with Alkyl Hydroperoxide Anions via Vicarious Nucleophilic Substitution of Hydrogen" by Mieczyslaw Makosza et al. listed in The Journal of Organic Chemistry vol. 55, No. 17©1990 American Society.
"Dealkylation of Activated Alkyl Aryl Ethers Using Lithium Chloride in Dimethylformamide" by Angela M. Bernard et al. listed in Communicats Apr. 1989, pp. 287–289.
"Boron Trihalide–Methyl Sulfide Complexes as Convenient Reagents for Dealkylation of Aryl Ethers" by Paul G. Willard et al. listed in Tetrahedron Letters vol. 21, pp. 3731–3734 ©Pergamon Press Ltd. 1980.
"*Preparation of 1,3–dihydroxy–4,6–diaminobenzene and Its Salts*" by Kato Kazufumi et al. listed in Chemical Abstracts vol. 113 (1989).
"Preparation of 4,6–dinitroresorcinol from 1,5–dichloro–2, 4–dinitrobenzene" by Rauner Wolfram et al listed in Chemical Abstracts vol. 70 (1976).
"*Preparation of 1,3–dihydroxy–4,6–diaminobenzene as material for poly(benzbisoxazoles)*" by Sato Tetsuo et al listed in Chemical Abstracts, vol. 112 (1975).

Primary Examiner—Allen J. Robinson
Assistant Examiner—Brian M. Burn

[57] ABSTRACT

The present invention relates to a method of cleaving arylethers such as arylethers represented by the formula:

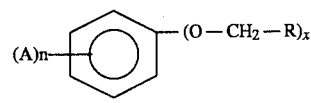

wherein R is hydrogen, $C_1$–$C_6$ alkyl, cycloalkyl, phenyl, substituted phenyl or $CH=CH_2$; each A is independently $NO_2$, hydroxy, halo, or methoxy; n is an integer from 0 to 5; and x is 1 or 2, comprising contacting the arylether with an amide hydrohalide salt under conditions sufficient to cleave the ether group(s) of the arylether and form a phenol or substituted phenol. The present invention also relates to a method of preparing 4,6-diaminoresorcinol, which is a monomer used for making polybenzoxazoles (PBO).

18 Claims, No Drawings

CLEAVING ARYLETHERS

BACKGROUND OF THE INVENTION

The present invention relates to a method for cleaving arylethers.

This method is used in processes for preparing 4,6-diaminoresorcinol, a monomer used in preparing polybenzoxazoles (PBO). Although there are a number of known methods for preparing 4,6-diaminoresorcinol, there continues to be a need to find more efficient and cost effective routes to obtain 4,6-diaminoresorcinol.

One known method involves synthesizing the monomer from 1,2,3-trichlorobenzene as described in U.S. Pat. No. 4,766,244 issued to Lysenko. However, 1,2,3-trichlorobenzene has limited availability.

Another method for preparing 4,6-diamino-resorcinol involves treating 1,3-dichloro-4,6-dinitrobenzene with base to form 4,6-dinitroresorcinol. Although 4,6-dinitroresorcinol may be reduced to form 4,6-diaminoresorcinol, the product recovery is prohibitively low for commercial value.

In yet another method, the appropriate arylether such as di-arylmethoxy-dinitrobenzene can be cleaved to produce 4,6-diaminoresorcinol. U.S. Pat. No. 5,072,053, issued to Blank et al., describes cleaving arylethers by converting di-arylmethoxydinitrobenzenes to 4,6-diaminoresorcinol by catalytic reduction using a platinum metal supported catalyst, which cleaves the diethers and reduces the nitro groups to amines. However, this described method also produces toluene as an unwanted by-product which must be removed or converted back to benzyl alcohol for recycle.

Other known methods for cleaving arylethers are described in *Protective Groups in Organic Chemistry* by Theodora W. Greene, pp. 88–100, 1981, J. Wiley & Sons using, for example hydrobromic acid or hydroiodic acid. Unfortunately, large amounts of hydrobromic acid or hydroiodic acid are required. In addition, when hydroiodic acid is used to cleave dinitroarylethers, e.g., methyl and benzyldinitroarylethers, the reaction is complicated in that the amines formed from the reduction of the nitro groups with iodide are subsequently alkylated by the alkyl iodide present. This reaction produces unwanted by-products, particularly when the desired product is 4,6-diaminoresorcinol used in benzoxazole polymerization.

In yet another method, as described in an article by Bernard et. al., in *Synthesis*, Apr. 1989, pp. 287–289, alkyl arylethers are cleaved using lithium chloride in an N,N-dimethylformamide solvent. However, this method requires a three-fold excess of lithium chloride which gives added expense to the method.

Accordingly, it remains highly desirable to provide a method for cleaving arylethers which does not have the disadvantages of the prior art.

SUMMARY OF THE INVENTION

Accordingly, in one aspect, the present invention is a method for cleaving arylethers comprising the step of contacting an arylether with an amide hydrohalide salt at conditions sufficient to cleave the ether group(s) of the arylether and form a phenol or substituted phenol.

In a second aspect, the present invention is a method for preparing 4,6-diaminoresorcinol comprising the steps of contacting a mono or diether of 4,6-dinitroresorcinol with an amide hydrohalide salt to form 4,6-dinitroresorcinol; and hydrogenating 4,6-dinitroresorcinol to form 4,6-diaminoresorcinol.

In one preferred embodiment for the preparation of arylethers used in preparing 4,6-diaminoresorcinol, a monoether of 4,6-dinitroresorcinol is prepared by contacting 1,3-dichloro-4,6-dinitrobenzene with an aqueous alcohol in the presence of hydroxide base. In a second preferred embodiment, a monoether of 4,6-dinitroresorcinol is prepared by contacting 2,4-dinitrochlorobenzene with a hydroperoxide in the presence of an anhydrous alkali metal hydroxide, and an alkyl alcohol or benzyl alcohol, to form a 5-alkoxy-2,4-dinitrophenol or a 5-benzyloxy-2,4-dinitrophenol. In yet another preferred embodiment, a diether of 4,6-dinitroresorcinol is prepared by contacting 1,3-dichloro-4,6-dinitrobenzene with i) a hydroxy-containing compound in the presence of hydroxide base or ii) an alkanolic metal alkoxide.

Using the method of the present invention, arylethers can be cleaved without the need for large amounts of hydrobromic acid, hydroiodic acid or lithium chloride and without the formation of unwanted by-products. The method of the present invention is particularly useful for the preparation of 4,6-diaminoresorcinol, a monomer used for making polybenzoxazoles (PBO).

DETAILED DESCRIPTION OF THE INVENTION

The term arylether as used in the present invention refers to any compound containing an aryl group which has been substituted by at least one ether group, including mono and diethers, such that upon cleavage of the ether groups a phenol or substituted phenol is formed. The arylethers used in the present invention may be any arylether which is stable under the reaction conditions and does not form undesirable by-products which would be detrimental to the reaction. Arylethers appropriate for the process of the present invention include but are not limited to arylethers of the formula:

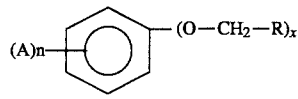

wherein R is hydrogen, $C_1$–$C_6$ alkyl, cycloalkyl, phenyl or substituted phenyl, $CH=CH_2$ or any organic moiety which will not be detrimental to the formation of the final product; each A is independently $NO_2$, hydroxy, halo, or methoxy; n is an integer from 0 to 5; and x is 1 or 2.

The preferred arylethers advantageously employed in the present invention include alkyl arylethers, branched alkyl arylethers, cycloalkyl arylethers, allyl arylethers and benzyl arylethers. Preferred arylethers correspond to the formula:

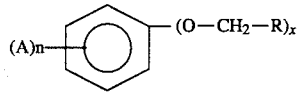

wherein R is hydrogen, $C_1$–$C_6$ alkyl, $C_3$–$C_6$ cycloalkyl, phenyl or substituted phenyl, or $CH=CH_2$; each A is independently $NO_2$, hydroxy, halo, or methoxy; n is an integer from 0 to 5; and x is 1 or 2. Preferably R is methyl, ethyl, allyl, hydrogen, phenyl or phenyl substituted with a halogen or an electron withdrawing group. More preferably R is phenyl, or hydrogen. Most preferably, R is hydrogen. Preferably, n is 0, 2 or 3 and each A is independently $NO_2$, hydroxy, halo, or methoxy. More preferably n is 3 and each A is independently NO$_2$, hydroxy, halo, or methoxy. Most preferably, n is 3, two of the A substituents are NO$_2$, and the third A is hydroxy or methoxy.

The arylethers used can be prepared by techniques well-known in the art for preparing such ethers. In one aspect of the present invention, 4,6-diaminoresorcinol is prepared. In one method of the present invention 4,6-diaminoresorcinol is prepared from the monoether of 4,6-dinitroresorcinol. The monoether of 4,6-dinitroresorcinol is advantageously prepared in one embodiment by contacting 1,3-dichloro-4,6-dinitrobenzene with an aqueous alkyl alcohol in the presence of hydroxide base, preferably sodium hydroxide, under conditions sufficient to produce a monoether, specifically 5-alkoxy-2,4-dinitrophenol. Similarly, 1,2,3-trichloro-4,6-dinitrobenzene may also be converted to 6-chloro-5-alkoxy-2,4-dinitrophenol under the same conditions. In another method 4,6-diaminoresorcinol is prepared from the diether of 4,6-dinitroresorcinol. A diether of 4,6-dinitroresorcinol can be similarly prepared by contacting 1,3-dichloro-4,6-dinitrobenzene or 1,2,3-trichloro-4,6-dinitrobenzene with a hydroxy-containing compound in the presence of hydroxide base, (greater amounts of hydroxy-containing compound can be employed than in preparing the monoether). Alternatively, the diether can be formed by contacting 1,3-dichloro-4,6-dinitrobenzene or 1,2,3-trichloro-4,6-dinitrobenzene with an alkanolic sodium alkoxide, preferably methanolic sodium methoxide, under conditions sufficient to produce a diether, specifically 1,3-dimethoxy-4,6-dinitrobenzene or 1,3-dimethoxy-2-chloro-4,6-dinitrobenzene. 1,3-Dichloro-4,6-dinitrobenzene can be prepared by the dinitration of m-dichlorobenzene as in Boyer and Buriks, *Organic Synthesis Collective Vol.* 5, pg. 1067, John Wiley & Sons Inc., N.Y. 1973 and 1,2,3-trichlorobenzene may be dinitrated under equivalent conditions.

The starting materials appropriate for preparing the arylethers used in the present invention include any hydroxy-containing compound which will form an ether when reacted with an aryl compound. The preferred hydroxy-containing compounds are benzyl alcohols, allyl alcohols, cylcoalkyl alcohols, and branched- or straight-chain C$_1$–C$_7$ alkyl alcohols, such as methanol, ethanol and propanol. More preferred are benzyl alcohol and alkyl alcohols, such as methanol and ethanol, wherein the most preferred is methanol or benzyl alcohol.

The alkanolic metal alkoxide which can be employed in preparing the dinitroarylether is an alkanolic solution containing an alkali metal alkoxide which can be prepared by dissolving an alkali metal in an alkanol. The alkanol may be a C$_1$–C$_7$ alkanol, is preferably C$_1$–C$_3$ alkanol and is most preferably methanol. The metal may be any alkali metal and is most preferably sodium. The solution may contain any effective amount of alkali metal but it preferably contains from about 20 to about 40, most preferably about 25 weight percent, said weight percent being based on the total weight of the solution.

In a second embodiment, the monoether of 4,6-dinitroresorcinol is advantageously prepared by contacting 1-chloro-2,4-dinitrobenzene with a hydroperoxide in the presence of an anhydrous alkali metal hydroxide, (as described in Makosza and Sienkiewicz, *Journal of Organic Chemistry*, Vol. 55 No. 17, Aug. 17, 1990, "Hydroxylation of Nitroarenes with Alkyl Hydroperoxide Anions via Vicarious Nucleophilic Substitution of Hydrogen"), and further reacted with an alkyl or benzyl alcohol to form a 5-alkoxy- or a 5-benzyloxy-2,4-dinitrophenol. The hydroperoxide may be any tertiary alkyl or aralkyl hydroperoxide. The term aralkyl refers to a radical in which an alkyl H atom is substituted by an aryl group. Preferred hydroperoxides are cumyl, tert-butyl, and neopentyl hydroperoxides. More preferred are cumene hydroperoxide and tert-butyl hydroperoxide. Most preferred is cumene hydroperoxide.

The alkali metal hydroxide is preferably sodium hydroxide, potassium hydroxide, lithium hydroxide or cesium hydroxide. More preferred is sodium hydroxide or potassium hydroxide, wherein the most preferred is sodium hydroxide.

In the practice of the present invention, the arylethers are cleaved using an amide hydrohalide salt. While the amide hydrohalide salt most advantageously employed in the practice of the present invention will depend on a number of different factors, including the desired product and the conditions of reaction, in general, the preferred amide hydrohalide salts used in the method of the present invention are tert-amide hydrochloride, hydrobromide or hydroiodide salts. A tert-amide is any compound containing a nitrogen atom bonded to three carbon atoms wherein one of the carbon atoms is part of a carbonyl group. The preferred tert-amide hydrohalide salts are the hydrohalide salts of N,N-dimethylformamide (DMF), cyclohexylpyrrolidinone, hexamethylpyrrolidinone, hexamethylphosphoramide, N,N-dimethylacetamide (DMAC) and N-methylpyrrolidinone (NMP). More preferred are the hydrochloride salts of N,N-dimethylformamide, cyclohexylpyrrolidinone, hexamethylpyrrolidinone, hexamethylphosphoramide, N,N-dimethylacetamide and N-methylpyrrolidinone. Most preferred is the hydrochloride salt of N,N-dimethylacetamide.

Methods for preparing amide hydrohalide salts are described in "Pyrrolidinecarboxaldehyde hydrohalide catalyzed halogenations of aliphatic alkdehydes," *Synth Commun.*, 15 (11), pp. 977–84, by Pews and Lysenko. In general, the amide hydrohalide salt is prepared from the corresponding amide by saturating the amide with an appropriate dry hydrogen halide gas. In most cases the salts are solids and may be isolated by filtration and stored or prepared and used in situ from the addition of the appropriate amount of hydrogen halide.

The arylether and the amide hydrohalide salt are used in amounts and at conditions sufficient to cleave the arylether group(s) and produce the desired phenol. While the relative amounts of the arylether and the amide hydrohalide salt most advantageously used can vary depending on a number of factors, including the specific arylether and amide hydrohalide salt employed, and the reaction conditions, it is generally preferable to use at least a stoichiometric amount and less than 1.5 equivalents of the hydrohalide salt per equivalent of the arylether. More preferably, the amide hydrohalide salt is used in an amount from 1.0 to about 1.2 equivalents per equivalent of arylether. Most preferably, the amide hydrohalide salt and arylether are employed in stoichiometric amounts. A stoichiometric amount of amide hydrohalide salt refers to the amount of amide hydrohalide salt needed to react with the reactive site or sites of the arylether, without excess, to produce the desired phenol.

Although the reaction may be conducted without a solvent under certain conditions, it is most preferably conducted in a solvent for the arylether, the amide hydrohalide salt and their reaction product. Any solvent for the arylether, amide hydrohalide salt, and their reaction product which does not significantly and adversely affect the reaction may be employed. Any polar aprotic solvent is advantageously employed in the method of the present invention. The preferred solvents are tert-amides. More preferred is a tert-amide corresponding to the amide hydrohalide salt, e.g., N,N-dimethylacetamide is used as the solvent when N,N-dimethylacetamide HCl salt is used in the reaction. Most preferred amide solvents include N,N-dimethyl-formamide, cyclohexylpyrrolidinone, hexamethylpyrrol-idinone, hexamethylphosphoramide, N,N-dimethylacetamide and N-methylpyrrolidinone. More preferred amide solvents include N,N-dimethylformamide, N,N-dimethyl-acetamide and N-methylpyrrolidinone.

The temperature and pressure at which the cleavage reaction is most advantageously conducted is dependent on many factors including the specific reactants and the desired reaction product. The cleavage reaction can be carried out at any temperature which is sufficient for the cleavage reaction to occur. Preferably, the reaction is carried out at a temperature from about 75° C. to about 180° C. More preferably, the reaction is conducted at temperatures from about 120° C. to about 140° C. and most preferably at a temperature of about 130° C. At these temperatures, the reaction generally requires from about 1 hour to about 30 hours. More preferably, the reaction is conducted from about 2 hours to about 24 hours and most preferably from about 3 hours to about 20 hours.

The pressures employed in the methods of the present invention will depend on many factors including the temperature, specific reactants and the product desired. Any pressure at which the cleavage reaction will occur is acceptable. The preferred method uses atmospheric pressure.

Following the cleavage reaction, the reaction product can be further reacted or recovered using conventional techniques such as removing the solvent from the reaction mixture, washing with HCl, extracting with ethyl acetate, drying and concentrating. In the preparation of 4,6-diaminoresorcinol by the method of the present invention, the cleaved reaction product is 4,6-dinitroresorcinol. 4,6-Dinitroresorcinol is then reduced and recovered most advantageously as a hydrochloride salt of 4,6-diaminoresorcinol. Hydrogenation of 4,6-dinitroresorcinol is well-known in the art and described in U.S. Pat. No. 4,912,246 issued to Lysenko et. al., which is incorporated herein by reference. Any hydrogenation process which will reduce nitro groups to amino groups can be used in the process of the present invention. In a preferred method, 4,6-dinitroresorcinol is reduced to 4,6-diaminoresorcinol by contacting it with a reducing agent, such as hydrogen gas in the presence of a reduction catalyst, such as palladium on carbon.

The following examples are set forth to illustrate the present invention and should not be construed to limit its scope. In the examples, all parts and percentages are by weight unless otherwise indicated.

EXAMPLES

Preparing Ethers of Dinitroresorcinol

Example 1—Preparing 5-Methoxy-2,4-dinitrophenol from 1,3-Dichloro-4,6-dinitrobenzene:

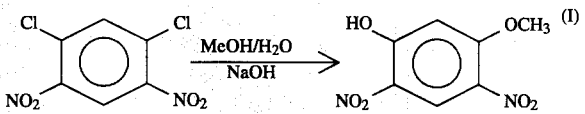

A 1-liter (L), round-bottom flask equipped with a mechanical stirrer and a reflux condenser is charged with 23.7 grams (g) of 1,3-dichloro-4,6-dinitrobenzene, 100 milliliters (mL) of methanol, 200 mL of water and 15 grams of sodium hydroxide and heated to approximately 65° C. for 8 hours. The reaction mixture is then poured into 0° C. aqueous hydrochloric acid, isolated by filtration and air-dried. The theoretical of 5-methoxy-2,4-dinitrophenol yield is 21.4 g, and the dry weight yield is 20.5 g which gives an overall 95% yield.

Example 2—Preparing 1,3-Dimethoxy-4,6-dinitrobenzene from 1,3-Dichloro-4,6-dinitrobenzene:

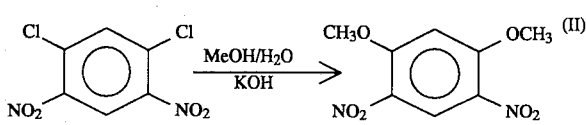

A 1-liter, 3-necked, round-bottomed flask is charged with 500 mL of methanol, 30 g of crushed potassium hydroxide, 75 mL of water, and 23.7 g (0.10 mole) of 1,3-dichloro-4,6-dinitrobenzene. The reaction mixture is agitated and heated to 65° C. for 8 hours and cooled to 25° C. The reaction mixture is then quenched with an excess of 0° C. aqueous hydrochloric acid. The resulting pale yellow solid is isolated by filtration and air-dried to yield 20 g (90% yield) of 1,3-dimethoxy-4,6-dinitrobenzene.

Example 3—Preparing 5-Methoxy-2,4-dinitrophenol from 2,4-Dinitro-chlorobenzene:

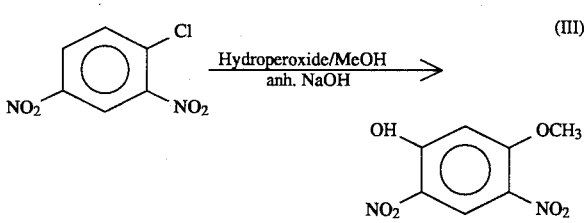

20 g of NaOH powder is added to a 250 mL 3-necked flask equipped with a mechanical stirrer, $CO_2$ condenser, dropping funnel and thermowell. Approximately 100–125 mL of liquid $NH_3$ are condensed into the reactor utilizing a dry ice bath. To the stirred slurry of powdered NaOH-$NH_3$ a solution of 1-chloro-2,4-dinitrobenzene (0.1 mol) and cumene hydroperoxide (0.1 mol) in 50 mL of methylene chloride is added dropwise over 1 hour maintaining the temperature at −30° C. by the refluxing $NH_3$.

After the addition is complete, the reaction mixture is allowed to warm to −10° C. to 0° C. and 75 mL of methanol containing 0.1 to 2 g of sodium hypophosphite is added dropwise over 1 hour. The resulting solution is agitated at room temperature for 3 to 4 hours.

The reaction mixture which contains precipitated Na phenolic salts is diluted with water to dissolve the salts and transferred to a 1-L separating funnel (to which a 500 mL solution of $H_2O$ has been added) where the aqueous solution is extracted with $CH_2Cl_2$ (2×200 mL) to remove the cumene derivatives. After extraction, the aqueous phenate salt solution is slowly acidified with concentrated HCl at a temperature of approximately 25° C. or less to precipitate the desired 5-methoxy-2,4-dinitrophenol. The crude phenol (17 to 19 g) is recrystallized from $H_2O$-MeOH (50:50) to give the preferred product in 75% to 80% yield.

Example 4—Preparing 5-Benzyloxy-2,4-dinitrophenol from 2,4-Dinitrochlorobenzene:

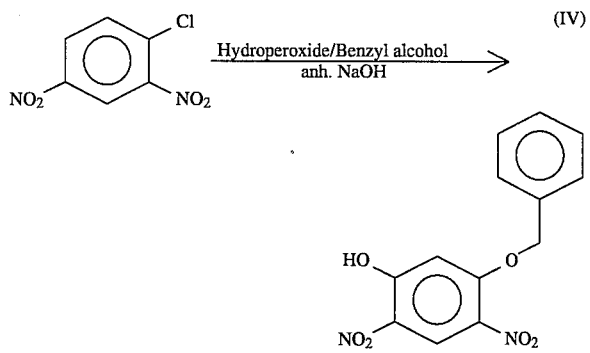

To a stirred slurry of powdered NaOH (20 g) in 125 mL of liquid $NH_3$ (−33° C.) contained in a 250 mL flask equipped with a mechanical stirrer, dropping funnel, thermometer and dry ice condenser, is added 1-chloro-2,4-dinitrobenzene (20.2 g), and 20 g of 80% cumene hydroperoxide in 50 mL of methylene chloride. After the addition is complete, the reaction mixture is allowed to warm to −10° C. and benzyl alcohol (75 mL) is added dropwise. The methylene chloride is removed in vacuo and the mixture is stirred overnight at approximately 25° C. The reaction mixture is then transferred to a separatory funnel containing 250 mL of $H_2O$ and is extracted twice with 50:50 toluene-:hexane (2×200 mL) to remove the unreacted benzyl alcohol and cumene residues. After acidification with concentrated HCl, the product is isolated by extraction in ethyl acetate. The organic extract is dried over $MgSO_4$ and evaporated. The residue is slurried in hot toluene (approximately 500 mL) and suction filtered through a small bed of silica to remove impurities. After evaporation of the toluene, the residue (approximately 12 g) is recrystallized from $CH_2Cl_2$-methanol to give a yellow solid, melting point (m.p.) 140° C./ to 142° C.

Preparation of 4,6-Dinitroresorcinol

Example 5

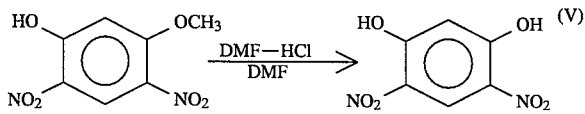

To a 100 mL round-bottom flask is added 2.14 g (10 mmol) of 5-methoxy-2,4-dinitrophenol (MDNP) and 1.31 g (12 mmol) of DMF-HCl in 30 mL of N,N-dimethylformamide (DMF). This mixture is stirred at 130° C. and monitored by High Pressure Liquid Chromatography (HPLC). After 8.5 hours essentially no MDNP is observed by HPLC. The reaction mixture is poured into 100 mL of 1N HCl, and extracted with ethyl acetate (EtOAc, 3×30 mL). The combined organics are washed with a single portion of 0.1N HCl, dried ($Na_2SO_4$) and concentrated by rotary evaporation to give crude 4,6-dinitroresorcinol (DNR) as a yellow solid (1.9 g, 95% yield): melting point (m.p.) 205° C. to 210° C., $^1H$ NMR ($CDCl_3$)δ11.03 (s,2H), 9.08 (s,1H), 6.82 (s,1H).

Example 6

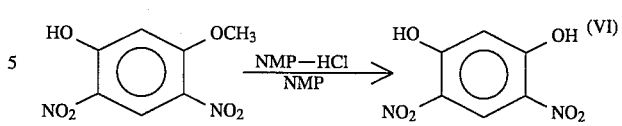

To a 100 mL round-bottom flask is added 2.50 g (12 mmol ) of MDNP and 3.25 g (24 mmol ) of NMP-HCl in 30 mL of N-methylpyrrolidinone (NMP). This mixture is stirred at 130° C. and monitored by HPLC. After 20 hours essentially no MDNP is observed by HPLC. The reaction mixture is poured into 50 mL of IN HCl, and extracted with EtOAc (2×50 mL). The combined organics are washed with a single portion of 0.3N HCl, dried ($Na_2SO_4$) and concentrated by rotary evaporation to give 4,6-dinitroresorcinol (DNR) as a yellow solid (3.1 g, 130% yield). $^1H$ NMR showed the product to contain a significant portion of NMP.

Example 7

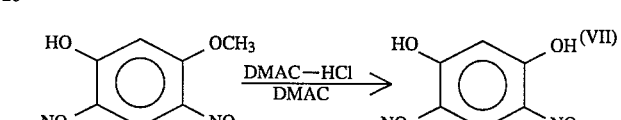

To a 100 mL round-bottom flask is added 4.00 g (19 mmol) of MDNP and 2.89 g (23 mmol) of DMAC-HCl in 15 mL of N,N-dimethylacetamide (DMAC). This mixture is stirred at 130° C. and monitored by HPLC. After 6.5 hours essentially no MDNP is observed by HPLC. The reaction mixture is poured into 160 mL of 1N HCl, and extracted with EtOAc (3×75 mL). The combined organics are washed with 0.3 N HCl, dried ($Na_2SO_4$) and concentrated by rotary evaporation to give 4,6-dinitroresorcinol (DNR) as a yellow solid (3.5 g, 92% yield).

Example 8

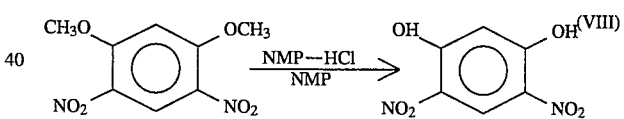

A 100 mL, 3-necked, round-bottom flask is charged with 30 mL of N-methylpyrrolidinone, 2.6 g (0.02 mole) of 1,3-dimethoxy-4,6-dinitrobenzene. The resulting solution is heated to 130° C. for two to three hours. The reaction mixture is then cooled and poured into an excess of dilute hydrochloric acid. The resulting solid is isolated by filtration to yield 1.9 g (95% yield) of 4,6-dinitroresorcinol.

Example 9—Preparation of 4,6-Diaminoresorcinol Dihydrochloride

A 1-L Hastalloy C autoclave, equipped with a gas dispersion turbine, sampling port, thermowell, and a cooling coil is charged with 50.0 g (0.25 mole) of 4,6-dinitroresorcinol, 380 g of n-propanol, 100 g of water, and 19.0 g of ammonium acetate. An aqueous slurry of 2.5 g of 10% Pd/C catalyst, is added and the reactor is sealed and purged with nitrogen. Hydrogen gas is charged to the reactor, and the pressure is cycled between 50 and 80 psig while maintaining the temperature of the reaction between about 50° C. to about 55° C. The progress of the reaction is monitored by hydrogen uptake. When no further hydrogen uptake is observed, the reactor is cooled to approximately 25° C. and 300 mL of concentrated HCl, containing 1.5 g stannous chloride dihydrate, is added to the black reaction mixture. The resultant gray solid is isolated by filtration and air-dried to yield 57.0 g of the crude dihydrochloride salt of the diaminoresorcinol which also contains the catalyst as an impurity.

Purification of 4,6-Diaminoresorcinol Dihydrochloride

The crude diaminoresorcinol (57.0 g), from Step A, containing the Pd/C catalyst, is dissolved in 400 g of 6% aqueous HCl at 80° C. The catalyst is removed by filtration. An additional 50.0 g of concentrated HCl containing 1.5 g of stannous chloride dihydrate is added to the diaminoresorcinol mixture along with 5.0 g of activated carbon. The solution is heated at reflux for 15 minutes and then the carbon is removed by filtration. The filtrate is cooled to 0° C. to allow crystallization of the product. The resulting white precipitate is isolated by filtration under a purge of dry nitrogen. This filter cake is then dried in vacuo at 40° C. to a constant weight to yield 48.7 g of essentially pure (99.8%) 4,6-diaminoresorcinol dihydrochloride having a m.p. of >300° C. Elemental Anal. calc'd for $C_6H_{10}Cl_2N_2O_2$ (213.0643): C, 33.82; H, 4.73; Cl, 33.28; N, 13.15; 0, 15.02, found: C, 33.6; H, 4.64; N, 13.20.

$^1$H NMR, DMSO $d_6$ (ppm); 6.95 (1 H,s), 7.48 (1 H,s), 9.56 (b.s.), 10.5 (b.s).

$^{13}$C NMR, DMSO $d_6$ (ppm); 103.69, 109.87, 119.48, 151.25.

What is claimed is:

1. A method of cleaving phenylethers comprising contacting the arylether with an amide hydrohalide salt under conditions sufficient to cleave the ether group(s) of the arylether and form a phenol or substituted phenol.

2. A method of claim 1 wherein the amide hydrohalide salt is an amide hydrochloride salt.

3. A method of claim 2 wherein the amide hydrochloride salt is selected from the group consisting of the hydrochloride salts of N,N-dimethylformamide, cyclohexylpyrrolidinone, hexamethylpyrrolidinone, hexamethylphosphoramide, N,N-dimethylacetamide and N-methylpyrrolidinone.

4. A method of claim 1 wherein the phenylether is contacted with the amide hydrohalide salt at a temperature between about 75° C. to about 180° C.

5. A method of cleaving arylethers corresponding to the formula:

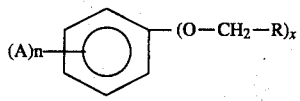

wherein R is hydrogen, $C_1$-$C_6$ alkyl, cycloalkyl, phenyl or substituted phenyl or $CH=CH_2$; each A is independently $NO_2$, hydroxy, halo, or methoxy; n is an integer from 0 to 5; and x is 1 or 2, comprising:

contacting the arylether with an amide hydrohalide salt under conditions sufficient to cleave the ether group(s) of the arylether and form a phenol or substituted phenol.

6. A method of claim 5 wherein the arylether is contacted with the amide hydrohalide salt at a temperature between about 75° C. to about 180° C.

7. A method of claim 5 wherein the arylether is an alkyl arylether.

8. A method of claim 7 wherein the alkyl arylether is a methyl arylether.

9. A method of claim 8 wherein the methyl arylether is 5-methoxy-2,4-dinitrophenol.

10. A method of claim 8 wherein the methyl arylether is 1,3-dimethoxy-4,6-dinitrobenzene.

11. A method of claim 5 wherein the arylether is a benzyl arylether.

12. A method of claim 11 wherein the benzyl arylether is 5-benzyloxy-2,4-dinitrophenol.

13. A method of claim 5 wherein the amide hydrohalide salt is an amide hydrochloride salt.

14. A method of claim 13 wherein the amide hydrochloride salt is selected from the group consisting of the hydrochloride salts of N,N-dimethylformamide, cyclohexylpyrrolidinone, hexamethylpyrrolidinone, hexamethylphosphoramide, N,N-dimethylacetamide and N-methylpyrrolidinone.

15. A method for preparing 4,6-diaminoresorcinol comprising the steps of:

A) contacting a compound of the formula:

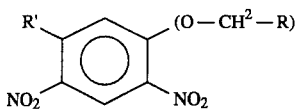

wherein R is hydrogen, $C_1$-$C_6$ alkyl, cycloalkyl, phenyl or substituted phenyl or $CH=CH_2$; and R' is selected from hydroxy, methoxy or $-O-CH_2-R$; with an amide hydrohalide salt to form a phenol or substituted phenol; and B) hydrogenating the phenol or substituted phenol to form 4,6-diaminoresorcinol.

16. A method of claim 15 wherein the amide hydrohalide salt is an amide hydrochloride salt.

17. A method of claim 16 wherein the amide hydrochloride salt is selected from the group consisting of the hydrochloride salts of N,N-dimethylformamide, cyclohexylpyrrolidinone, hexamethylpyrrolidinone, hexamethylphosphoramide, N,N-dimethylacetamide and N-methylpyrrolidinone.

18. A method of claim 15 wherein the arylether is contacted with the amide hydrohalide salt at a temperature between about 75° C. to about 180° C.

* * * * *